United States Patent [19]

Hirako et al.

[11] Patent Number: 5,856,520
[45] Date of Patent: Jan. 5, 1999

[54] SUBSTITUTED BENZENEDITHIOL METAL COMPLEX

[75] Inventors: Kazuyoshi Hirako; Satoshi Kimura; Michio Suzuki, all of Kako-gun, Japan

[73] Assignee: Sumitomo Seika Chemicals Co., Ltd., Hyogo, Japan

[21] Appl. No.: 945,077

[22] PCT Filed: Mar. 17, 1997

[86] PCT No.: PCT/JP97/00858

§ 371 Date: Oct. 20, 1997

§ 102(e) Date: Oct. 20, 1997

[87] PCT Pub. No.: WO97/34903

PCT Pub. Date: Sep. 25, 1997

[30] Foreign Application Priority Data

Mar. 21, 1996 [JP] Japan .................................. 8-093113
Jul. 31, 1996 [JP] Japan .................................. 8-219408
Jul. 31, 1996 [JP] Japan .................................. 8-219409

[51] Int. Cl.$^6$ ..................... C07D 327/00; C07D 401/00; C07D 295/00; G03C 1/492
[52] U.S. Cl. .............................. 549/3; 546/187; 544/109; 544/145; 430/270.1; 430/372; 430/517
[58] Field of Search ................................. 549/3; 544/109, 544/145; 546/187; 430/270.1, 372, 517

[56] References Cited

U.S. PATENT DOCUMENTS 5,512,416  4/1996  Namba et al. ..................... 430/270.21

FOREIGN PATENT DOCUMENTS 59-24692    2/1984   Japan .
59-55794    3/1984   Japan .
60-20991    2/1985   Japan .
60-36190    2/1985   Japan .
60-54892    3/1985   Japan .
63-307854  12/1988   Japan .

Primary Examiner—Deborah C. Lambkin
Attorney, Agent, or Firm—Pollock, Vande Sande & Amernick

[57] ABSTRACT

A novel substituted benzenedithiol metal complex represented by the general formula (1) is provided. The substituted benzenedithiol metal complex is useful as a singlet oxygen quencher and as an optical data recording medium per se.

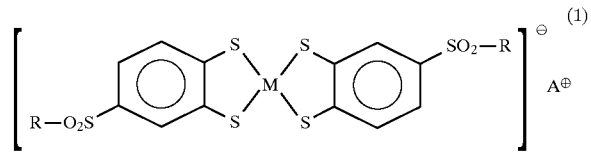

wherein M is a transition metal; $A^+$ is a quaternary ammonium group; and R is an organic group selected from the group consisting of organic groups represented by the formulae (i), (ii), (iii) and (iv):

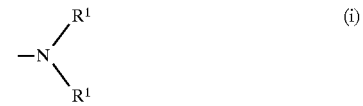

(wherein $R^1$ is an alkyl group having 1 to 4 carbon atoms),

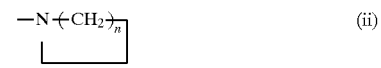

(wherein n is 3, 4 or 5),

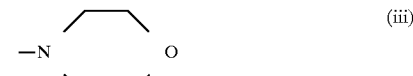

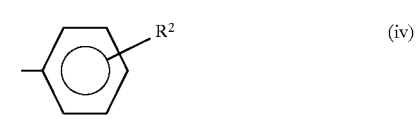

(wherein $R^2$ is one of a hydrogen atom and a substitutent having 1 to 4 carbon atoms).

16 Claims, No Drawings

SUBSTITUTED BENZENEDITHIOL METAL COMPLEX

This application is a 371 of PCT/JP97/00858 Mar. 17, 1997.

TECHNICAL FIELD

The present invention relates to a metal complex, more particularly, to a substituted benzenedithiol metal complex.

BACKGROUND ART

Indolenine cyanine dyes which are excellent in heat resistance and water resistance are advantageously used as optical data recording media constituting recording layers of various optical recording disks (see, for example, Japanese Unexamined Patent Publication No. 59-24692 (1984)). However, the indolenine cyanine dyes are liable to cause data reproduction deterioration due to repeated light irradiation for data reproduction and to cause photo-deterioration during storage in light and, hence, it is difficult to keep a recording layer employing such an indolenine cyanine dye stable during a prolonged use. Therefore, where an indolenine cyanine dye is used to form a recording layer, a metal complex capable of functioning as a singlet oxygen quencher is mixed with the indolenine cyanine dye, and a coating solution prepared by dissolving the mixture in a solvent is applied onto a resin substrate of an optical recording disk for the formation of the recording layer (see, for example, Japanese Unexamined Patent Publication No. 59-55794 (1984)).

If such a metal complex is capable of functioning not only as a singlet oxygen quencher but also as an optical data recording medium per se, the metal complex would be expected to have an enhanced usefulness. For example, a recording layer of an optical recording disk can be formed of the metal complex alone without the use of the indolenine cyanine dye.

It is therefore an object of the present invention to provide a novel metal complex which is capable of functioning not only as a singlet oxygen quencher but also as an optical data recording medium per se.

DISCLOSURE OF THE INVENTION

A substituted benzenedithiol metal complex according to the present invention is represented by the following general formula (1):

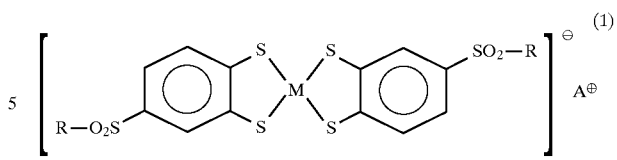

In the general formula (1), M is a transition metal, $A^+$ is a quaternary ammonium group, and R is an organic group selected from the group consisting of groups represented by the following formulae (i), (ii), (iii) and (iv):

(wherein $R^1$ is an alkyl group having 1 to 4 carbon atoms),

(wherein n is 3, 4 or 5),

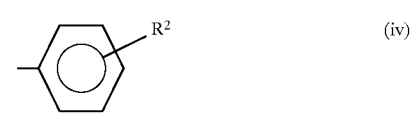

(wherein $R^2$ is one of a hydrogen atom and a substituent having 1 to 4 carbon atoms).

Specific examples of the substituted benzenedithiol metal complex include a 4-N,N-diethylsulfamoyl-1,2-benzenedithiol metal complex represented by the following general formula (1-a), a 4-piperidylsulfonyl-1,2-benzenedithiol metal complex represented by the following general formula (1-b), a 4-morpholinosulfonyl-1,2-benzenedithiol metal complex represented by the following general formula (1-c), and a 4-phenylsulfonyl-1,2-benzenedithiol metal complex represented by the following general formula (1-d).

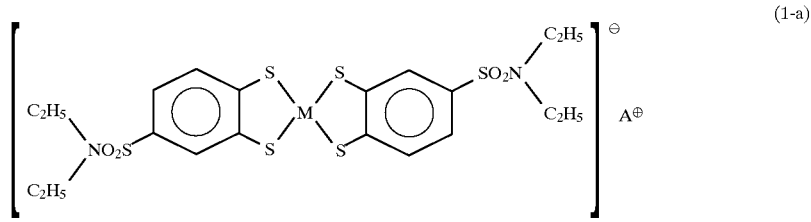

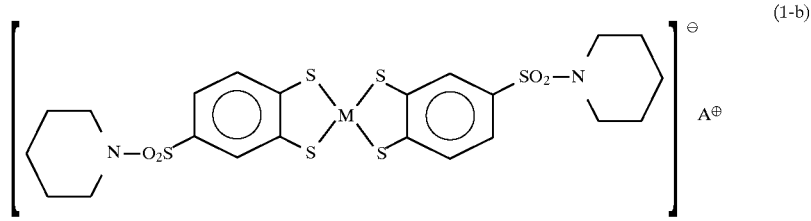

-continued

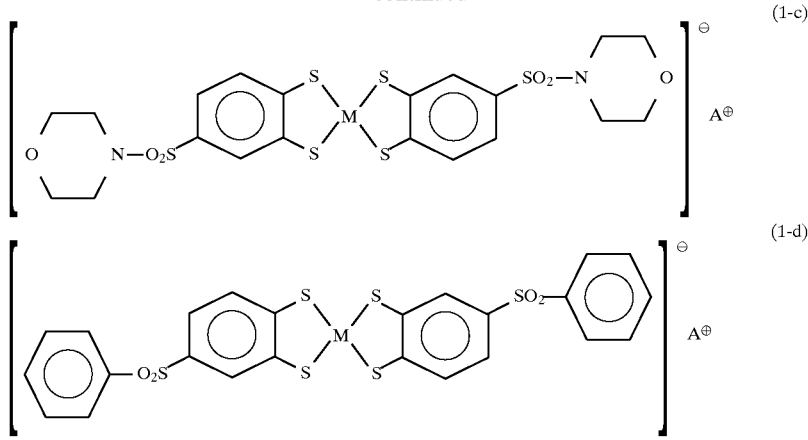

In the general formulae (1-a), (1-b), (1-c) and (1-d), M and A$^+$ are the same as in the general formula (1).

A preparation process for the substituted benzenedithiol metal complex represented by the general formula (1) in accordance with the present invention includes the following steps:

⊚ Reacting 3,4-dibromobenzenesulfonyl chloride with a compound selected from the group consisting of compounds represented by the following general formulae (a), (b), (c) and (d) to synthesize 4-substituted sulfonyl-1,2-dibromobenzene represented by the following general formula (2):

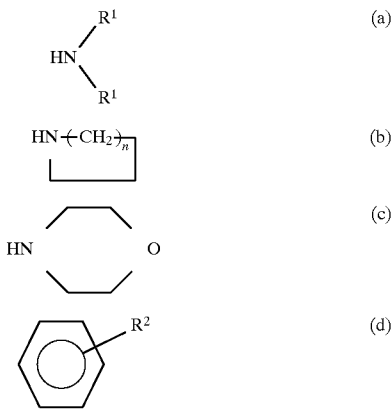

wherein R$^1$, n and R$^2$ are the same as in the general formula (i), (ii) and (iv),

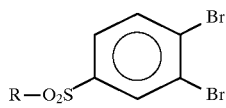

wherein R is the same as in the general formula (1);

⊚ Converting the 4-substituted sulfonyl-1,2-dibromobenzene into a 4-substituted sulfonyl-1,2-benzenedithiol represented by the following general formula (3):

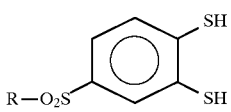

wherein R is the same as in the general formula (2); and

⊚ Reacting the 4-substituted sulfonyl-1,2-benzenedithiol with a transition metal salt and a quaternary ammonium salt.

Where R in the substituted benzenedithiol metal complex represented by the general formula (1) is an aryl group represented by the formula (iv), the substituted benzenedithiol metal complex can be prepared through another preparation process including the following steps:

⊚ Preparing a solution by dissolving 3,4-dibromobenzenesulfonyl chloride in a compound represented by the following general formula (d):

wherein R$^2$ is one of a hydrogen atom and a substituent having 1 to 4 carbon atoms;

⊚ Adding aluminum chloride to the solution and reacting 3,4-dibromobenzenesulfonyl chloride with the compound represented by the general formula (d) to synthesize 4-arylsulfonyl-1,2-dibromobenzene;

⊚ Converting the 4-arylsulfonyl-1,2-dibromobenzene into 4-arylsulfonyl-1,2-benzenedithiol; and ⊚ Reacting the 4-arylsulfonyl-1,2-benzenedithiol with a transition metal salt and a quaternary ammonium salt.

Further another preparation process for the substituted benzenedithiol metal complex represented by the general formula (1) according to the present invention includes the step of reacting the substituted benzenedithiol compound represented by the general formula (3) with a transition metal salt and a quaternary ammonium salt.

The substituted benzenedithiol metal complex according to the present invention is useful as a singlet oxygen quencher and as an optical data recording medium.

The present invention also provides a 4-substituted sulfonyl-1,2-dibromobenzene represented by the general formula (2), wherein R is an aryl group represented by the formula (iv) which is shown as an organic group in the general formula (1). A preparation process for the 4-substituted sulfonyl-1,2-dibromobenzene according to the present invention includes the steps of preparing a solution by dissolving 3,4-dibromobenzenesulfonyl chloride in the compound represented by the general formula (d), adding aluminum chloride to the solution, and reacting 3,4-dibromobenzenesulfonyl chloride with the compound represented by the general formula (d).

The present invention also provides the 4-substituted sulfonyl-1,2-benzenedithiol represented by the general formula (3). A preparation process for the 4-substituted sulfonyl-1,2-benzenedithiol according to the present invention includes the step of reacting the 4-substituted sulfonyl- 1,2-dibromobenzene represented by the general formula (2) with sodium hydrosulfide in the presence of catalysts of iron powder and sulfur powder.

The 4-substituted Sulfonyl-1,2-dibromobenzene and the 4-substituted sulfonyl-1,2-benzenedithiol according to the present invention are useful as materials for the preparation of the substituted benzenedithiol metal complex.

Other objects and effects of the present invention will become apparent from the following detailed description.

DETAILED DESCRIPTION OF THE PRESENT INVENTION

The substituted benzenedithiol metal complex of the present invention is represented by the following general formula (1):

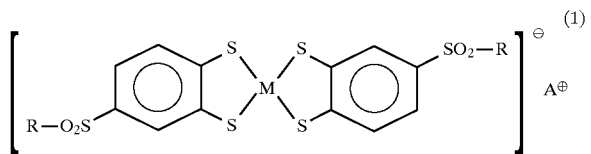
(1)

wherein R is an organic group represented by the following formula (i), (ii), (iii) or (iv):

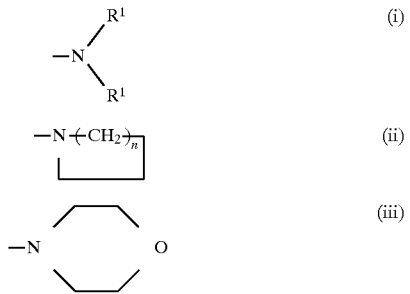

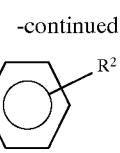
(iv)

In the formula (i), $R^1$ is an alkyl group having 1 to 4 carbon atoms, and examples thereof include methyl, ethyl, propyl, iso-propyl, n-butyl, tert-butyl and sec-butyl. In the formula (ii), n is an integer, more specifically, 3, 4 or 5. The organic group represented by the formula (iv) is an aryl group. In the formula (iv), $R^2$ is a hydrogen atom or a substitutent having 1 to 4 carbon atoms, and examples thereof include hydrocarbon groups such as methyl, ethyl, propyl, iso-propyl, n-butyl, tert-butyl and sec-butyl.

The general formula (1) includes two organic groups R, which may be either the same or different.

In the general formula (1), M is a transition metal, which is not particularly limited but examples thereof include copper, cobalt and nickel.

In the general formula (1), $A^+$ is a quaternary ammonium group, and examples thereof include tetra-n-butylammonium group, tetraethylammonium group, tetraphenylammonium group, tetrabenzylammonium group and trimethylbenzylammonium group.

Specific examples of the substituted benzenedithiol metal complex represented by the general formula (1) include a 4-N,N-diethylsulfamoyl-1,2-benzenedithiol metal complex represented by the following general formula (1-a), a 4-piperidylsulfonyl-1,2-benzenedithiol metal complex represented by the following general formula (1-b), a 4-morpholinosulfonyl-1,2-benzenedithiol metal complex represented by the following general formula (1-c), and a 4-phenylsulfonyl-1,2-benzenedithiol metal complex represented by the following general formula (1-d). In the general formulae (1-a), (1-b), (1-c) and (1-d), M and $A^+$ are the same as in the general formula (1).

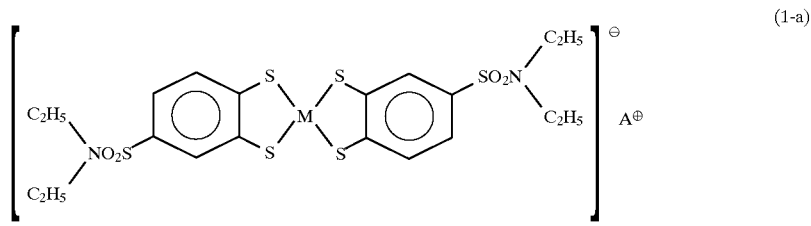
(1-a)

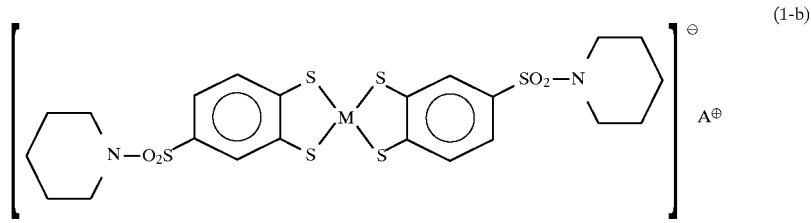
(1-b)

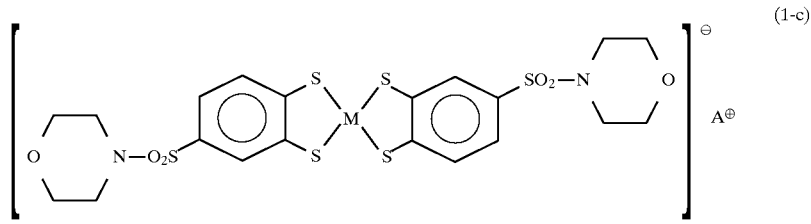
(1-c)

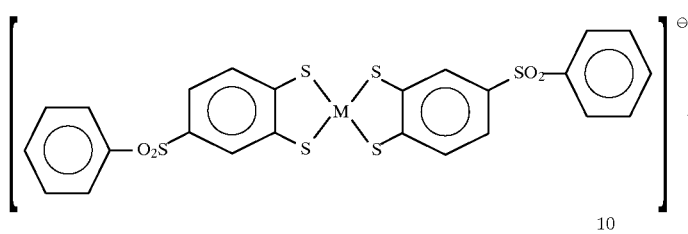

(1-d)

There will next be described a preferable preparation process for the substituted benzenedithiol metal complex represented by the general formula (1).

The substituted benzenedithiol metal complex represented by the general formula (1) can be synthesized from an intermediate product synthesized from a starting material of 1,2-dibromobenzene. An explanation will hereinafter be given to respective steps of the preparation process.

Step 1

In this step, 1,2-dibromobenzene is reacted with fuming sulfuric acid in a solvent to synthesize 3,4-dibromobenzenesulfonic acid.

Fuming sulfuric acid is preferably used in an amount of 1.0 to 2.0 times in mol, more preferably 1.1 to 1.5 times in mol, relative to the amount of 1,2-dibromobenzene on an $SO_3$ basis. Examples of the solvent to be preferably used in this reaction include halogenated hydrocarbon solvents such as chloroform, carbon tetrachloride and 1,2-ethylene dichloride.

The reaction temperature is preferably controlled in a range from 50° to 100° C., more preferably from 65° to 80° C. The optimal reaction time varies depending on the reaction temperature, but is typically 1 to 4 hours.

Step 2

For synthesis of 3,4-dibromobenzenesulfonyl chloride, 3,4-dibromobenzenesulfonic acid obtained in Step 1 is reacted with thionyl chloride.

Thionyl chloride is typically used in an amount of 1.0 to 2.5 times in mol, preferably 1.5 to 2.2 times in mol, relative to the amount of 3,4-dibromobenzenesulfonic acid.

As in Step 1, a halogenated hydrocarbon solvent such as chloroform, carbon tetrachloride and 1,2-ethylene dichloride is preferably used in this reaction. The use of the same solvent as in Step 1 is advantageous in terms of operation efficiency, yield and the like because the reactions are allowed to take place sequentially. Where the organic group R in the metal complex to be prepared is an aryl group, i.e., the organic group R in the general formula (1) is represented by the formula (iv), and benzene is used as the compound of the general formula (d) in the subsequent Step 3, it is preferred to use benzene as the solvent in this step. Thus, this step and the subsequent step can sequentially be performed, so that the use of benzene as the solvent is advantageous in terms of operation efficiency, yield and the like.

The reaction temperature in this step is preferably 50° to 100° C., more preferably 55° to 80° C. The optimal reaction time varies depending on the reaction temperature, but is typically 1 to 4 hours.

Step 3

This step is partially different between a case where the organic group R in the general formula (1) is represented by the formula (i), (ii) or (iii) and a case where the organic group R is represented by the formula (iv). Therefore, an explanation will be given to each of the cases employing different types of organic groups R.

⊙ Case where the organic group R in the general formula (1) is represented by the formula (i), (ii) or (iii)

For synthesis of 4-substituted sulfonyl-1,2-dibromobenzene, 3,4-dibromobenzenesulfonyl chloride obtained in Step 2 is reacted with a compound represented by the general formula (a) or (b) or morpholine represented by the formula (c) The groups $R^1$ in the general formula (a) and the number n in the general formula (b) are the same as in the formulae (i) and (ii).

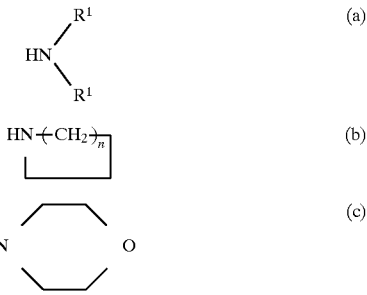

For preparation of a metal complex including an organic group R represented by the formula (i) in the general formula (1), e.g., a 4-N,N-diethylsulfamoyl-1,2-benzenedithiol metal complex represented by the general formula (1-a), diethylamine is used as the compound of the general formula (a), in which $R^1$ is ethyl. For preparation of a metal complex including an organic group R represented by the formula (ii) in the general formula (1), e.g., a 4-piperidylsulfonyl-1,2-benzenedithiol metal complex represented by the general formula (1-b), piperidine is used as the compound of the general formula (b), in which n is 5. For preparation of a metal complex including an organic group R represented by the formula (iii) in the general formula (1), e.g., a 4-morpholinosulfonyl-1,2-benzenedithiol metal complex represented by the general formula (1-c) morpholine of the formula (c) is used.

The compound represented by the general formula (a) or (b) or morpholine of the formula (c) is used in this reaction, typically, in an amount of 1.5 to 4.0 times in mol, preferably 2.0 to 3.0 times in mol, relative to the amount of 3,4-dibromobenzenesulfonic acid used in Step 2.

As in Step 2, a halogenated hydrocarbon solvent such as chloroform, carbon tetrachloride and 1,2-ethylene dichloride is preferably used in this reaction. The use of the same solvent as in Step 2 is advantageous in terms of operation efficiency, yield and the like because the reactions are allowed to take place sequentially. The reaction temperature is preferably 15° to 40° C., more preferably 20° to 30° C. The optimal reaction time varies depending on the reaction temperature, but is typically 1 to 3 hours.

⊙ Case where the organic group R in the general formula (1) is represented by the formula (iv)

For synthesis of 4-arylsulfonyl-1,2-dibromobenzene (i.e., 4-substituted sulfonyl-1,2-dibromobenzene), 3,4-dibromobenzenesulfonyl chloride obtained in Step 2 is dissolved in a compound represented by the following general formula (d), then aluminum chloride is added to the resulting solution, and 3,4-dibromobenzenesulfonyl chloride is reacted with the compound represented by the general formula (d). In the general formula (d), $R^2$ is the same as in the formula (iv).

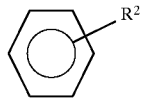

For preparation of a metal complex including phenyl as the organic group R in the general formula (1), i.e., a 4-phenylsulfonyl-1, 2-benzenedithiol metal complex represented by the general formula (1-d), benzene is used as the compound of the general formula (d), in which $R^2$ is hydrogen.

In this reaction, the compound represented by the general formula (d) is typically used in an amount of 1.0 or greater times in mol relative to the amount of 3,4-dibromobenzenesulfonyl chloride obtained in Step 2. Considering that the compound also serves as the solvent, the amount thereof is preferably 8.0 to 15.0 times in mol.

In this step, aluminum chloride is preferably used in an amount of 0.5 to 2.5 times in mol, more preferably 1.0 to 1.5 times in mol, relative to the amount of 3,4-dibromobenzenesulfonyl chloride.

The reaction temperature in this step is preferably 15° to 40° C., more preferably 20° to 30° C. The optimal reaction time varies depending on the reaction temperature, but is typically 1 to 3 hours.

The 4-substituted sulfonyl-1,2-dibromobenzene obtained in this step is represented by the following general formula (2). In the general formula (2), R is as defined by the formula (i), (ii), (iii) or (iv).

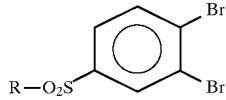

Step 4

Bromine atoms of the 4-substituted sulfonyl-1,2-dibromobenzene obtained in Step 3 are replaced with mercapto groups to synthesize a 4-substituted sulfonyl-1,2-benzenedithiol represented by the following general formula (3) More specifically, the 4-substituted sulfonyl-1,2-dibromobenzene is converted into the 4-substituted sulfonyl-1,2-benzenedithiol in this Step. In the general formula (3), R is the same as in the general formula (2).

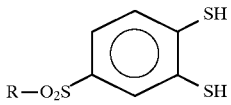

The replacement of the bromine atoms with the mercapto groups can be achieved by a method disclosed in Japanese Unexamined Patent Publication No. 6-25151 (1994) or No. 5-117225 (1993). More specifically, the 4-substituted sulfonyl-1,2-dibromobenzene obtained in Step 3 is reacted with sodium hydrosulfide in the presence of catalysts of iron powder and sulfur powder to give a 4-substituted sulfonyl-1,2-benzenedithiol as a target compound.

Sodium hydrosulfide is typically used in an amount of 1.5 to 4.0 times in mol, preferably 1.8 to 2.5 times in mol, relative to the amount of the 4-substituted sulfonyl-1,2-dibromobenzene. The iron powder as the catalyst is typically used in an amount of 0.4 to 2.0 times in mol, preferably 0.5 to 1.0 time in mol, relative to the amount of the 4-substituted sulfonyl-1,2-dibromobenzene. The sulfur powder as the catalyst is used in an amount of 1.0 to 20.0 wt %, preferably 1.0 to 5.0 wt %, relative to the 4-substituted sulfonyl-1,2-dibromobenzene.

The reaction temperature in this step is preferably 60° to 140° C., more preferably 70° to 120° C.

Step 5

The 4-substituted sulfonyl-1,2-benzenedithiol obtained in Step 4 is reacted with a transition metal salt and a quaternary ammonium salt in a lower alcohol to give the substituted benzenedithiol metal complex represented by the general formula (1).

Examples of specific lower alcohols to be herein used include methanol, ethanol, isopropanol and tert-butanol, among which methanol is preferred in terms of economy.

Used as the transition metal salt is a salt of the transition metal (m) contained in the substituted benzenedithiol metal complex of the general formula (1) to be prepared. Examples of specific transition metal salts include transition metal halides such as copper (II) chloride, cobalt chloride, nickel (II) chloride, copper (II) bromide, cobalt bromide, cobalt iodide and nickel iodide, transition metal nitrates such as copper nitrate and cobalt nitrate, transition metal sulfates such as copper sulfate and cobalt sulfate, and transition metal acetates such as copper acetate and cobalt acetate. Transition metal halides, particularly transition metal chlorides, are preferred in terms of economy, reactivity and the like.

The transition metal salt is preferably used in an amount of 0.3 to 10 times in mol relative to the amount of the 4-substituted sulfonyl-1,2-benzenedithiol. An amount of less than 0.3 times in mol results in a reduced yield and, conversely, an amount of greater than 10 times in mol is uneconomical because the yield is not increased.

Used as the quaternary ammonium salt is a salt of the quaternary ammonium group $(A^+)$ included in the substituted benzenedithiol metal complex of the general formula (1) to be prepared. Examples thereof include tetra-n-butylammonium bromide, tetra-n-butylammonium chloride, tetraethylammonium bromide, tetraethylammonium chloride, tetraphenylammonium bromide (tetraphenylammonium chloride, tetrabenzylammonium bromide, tetrabenzylammonium chloride, trimethylbenzylammonium bromide, trimethylbenzylammonium chloride and the like. Among these quaternary ammonium salts, tetra-n-butylammonium bromide, tetra-n-butylammonium chloride, tetraethylammonium bromide and tetraethylammonium chloride are preferred in terms of economy, reactivity and the like.

The quaternary ammonium salt is preferably used in an amount of 0.3 to 1.0 time in mol, more preferably 0.4 to 0.9 times in mol, relative to the amount of the 4-substituted sulfonyl-1,2-benzenedithiol. An amount of less than 0.3 times in mol results in a reduced yield and, conversely, an amount of greater than 1.0 time in mol is uneconomical because the yield is not increased.

To increase the yield, the reaction in this step is preferably allowed to react in the presence of an alkoxide. Examples of usable alkoxides include sodium methylate, sodium ethylate, potassium tert-butylate and the like, among which sodium methylate is preferred in terms of economy.

Where such an alkoxide is used, the amount thereof is preferably 1.5 to 10 times in mol, more preferably 2.0 to 3.0 times in mol, relative to the amount of the 4-substituted sulfonyl-1,2-benzenedithiol. If the amount is less than 1.5 times in mol, it is difficult to increase the yield. Conversely, an amount of greater than 10 times in mol is uneconomical because the yield is not increased.

Where the organic group R in the 4-substituted sulfonyl-1,2-benzenedithiol of the general formula (3) obtained in Step 4 is represented by the formula (i), (ii) or (iii), the reaction temperature in this step is preferably 15° to 40° C., more preferably 20° to 35° C. Where the organic group R in the general formula (3) is represented by the formula (iv), the reaction temperature is preferably 60° to 100° C., more preferably 65° to 90° C. The optimal reaction time varies depending on the reaction temperature, but is typically 1 to 3 hours.

The substituted benzenedithiol metal complex of the present invention obtained through the process steps described above is useful as a singlet oxygen quencher. Therefore, an optical recording disk having a recording layer which is less liable to data reproduction deterioration due to repeated light irradiation for data reproduction and to photo-deterioration during storage in light can be provided by mixing the substituted benzenedithiol metal complex of the present invention with an indolenine cyanine dye as an optical recording medium.

Further, the substituted benzenedithiol metal complex of the present invention itself functions as a material for an optical data recording medium and, therefore, a recording layer for an optical recording disk can be formed of the metal complex alone.

Where the formation of the recording layer for the optical recording disk is achieved by using the substituted benzenedithiol metal complex of the present invention, the metal complex alone or a mixture of the metal complex and an indolenine cyanine dye is dissolved in a solvent such as an alcohol for preparation of a coating solution, and then the coating solution is applied onto a resin substrate of the optical recording disk. At this time, the coating solution can readily be prepared because the substituted benzenedithiol metal complex of the present invention, particularly the metal complex containing the organic group R represented by the formula (i), (ii) or (iii) in the general formula (1), is highly soluble in a solvent such as an alcohol.

The present invention will hereinafter be described in detail by way of examples thereof.

EXAMPLE 1

Preparation of Substituted Benzenedithiol Metal Complex

A 300-ml four-neck flask equipped with a stirring device, a condenser and a thermometer was prepared. Then, 120 g of 1,2-ethylene dichloride and 76 g (0.32 mols) of 1,2-dibromobenzene were placed in the flask, and 56 g (0.42 mols) of 60% fuming sulfuric acid was added thereto dropwise in a gentle stream of nitrogen gas and allowed to react therewith at 70° C. for 2 hours. After the resulting reaction product solution was cooled, a reaction product was filtered out and then dried. Thus, 95 g of crude 3,4-dibromobenzenesulfonic acid was obtained.

In turn, a 500-ml four-neck flask equipped with a stirring device, a condenser and a thermometer was prepared. Then, 95 g of the thus obtained crude 3,4-dibromobenzenesulfonic acid, 225 g of 1,2-ethylene dichloride and 28.5 g of N,N-dimethylformamide were placed in the flask, and 73 g (0.61 mols) of thionyl chloride was added thereto dropwise and allowed to react therewith at 60° to 65° C. for 1 hour. After being cooled to room temperature, the resulting reaction product solution was added dropwise to 460 g of water and stirred therein at 0° to 10° C. for 0.5 hours.

The aqueous layer and organic layer of the resulting reaction product solution were separated, and the aqueous layer was removed. Then, 58 g (0.79 mols) of diethylamine was added dropwise to 290 g of the resulting organic layer, and was allowed to react at room temperature for 1 hour. In turn, 200 g of water was added to the resulting reaction mixture. Then, the resulting aqueous layer and organic layer were separated and, after the aqueous layer was removed, the solvent was distilled off under reduced pressure. Thus, 87 g of 4-N,N-diethylsulfamoyl-1,2-dibromobenzene was obtained. The yield was 73%.

Subsequently, 50 g of N,N-dimethylformamide, 1.2 g (0.022 mols) of iron powder and 0.4 g (0.013 mols) of sulfur powder were added to 10 g of 4-N,N-diethylsulfamoyl-1,2-dibromobenzene thus obtained. Then, a solution containing 5.0 g (0.062 mols) of 70% sodium hydrosulfide dissolved in 50 g of N,N-dimethylformamide was added dropwise to the resulting mixture, and was allowed to react at 95° C. for 2 hours.

In turn, 30 g of a 10% sodium methylate - methanol solution (containing 0.056 mols of sodium methylate) was added dropwise to the resulting solution, which was stirred for 1 hour. Then, a solution containing 3.2 g (0.014 mols) of nickel (II) chloride hexahydrate dissolved in 10 g of methanol was added dropwise to the resulting solution, and was allowed to react at 72° C. for 1 hour. After the reaction solution was cooled to room temperature, 14.6 g of a 31% tetrabutylammonium bromide-methanol solution (containing 0.014 mols of tetrabutylammonium bromide) was added dropwise to the reaction solution, and was allowed to react for 2 hours at room temperature with stirring.

The resulting reaction solution was concentrated, and purified through silica gel column chromatography. Fractions were concentrated to give 5.2 g of a dark green solid of 4-N,N-diethylsulfamoyl-1,2-benzenedithiol nickel complex as a target substance. The yield was 45% with respect to 4-N,N-diethylsulfamoyl-1,2-dibromobenzene. The 4-N,N-diethylsulfamoyl-1,2-benzenedithiol nickel complex thus obtained had a structural formula as shown below:

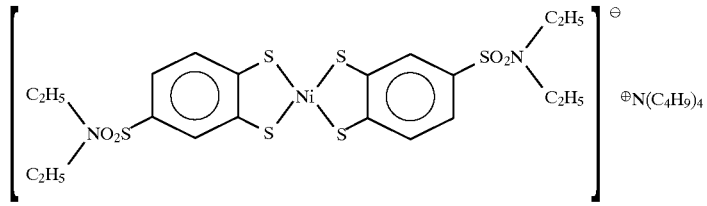

Analysis results and physical properties of the 4-N,N-diethylsulfamoyl-1,2-benzenedithiol nickel complex thus obtained are shown below:

| HPLC 99.4% Elemental analysis | | | | | |
|---|---|---|---|---|---|
| | C | H | N | S | Ni |
| Calculated value | 50.75 | 7.33 | 4.93 | 22.58 | 6.89 |
| Measured value | 50.1 | 7.1 | 4.9 | 22.3 | 6.91 |

Melting point 33.4° C. (DSC)
Ultraviolet and visible absorption spectrum
(solvent: methylene chloride)
Maximum absorption wavelength (nm)  861.6, 368.1, 315.9, 259.9
Molar absorption coefficient   13382, 11757, 36710, 42716
Infrared absorption spectrum (KBr, cm$^{-1}$)
2961.2, 2933.2, 2872.5, 2361.4, 1466.6, 1465.7, 1380.8, 1354.8,
1328.7, 1296.9, 1157.1, 1014.4, 931.5, 819.6, 712.6, 694.3, 610.4
Solubility (g/100 g-MeOH 25° C.) 0.52 g

EXAMPLE 2

Preparation of Substituted Benzenedithiol Metal Complex

The preparation process was performed in substantially the same manner as in EXAMPLE 1 except that 2.3 g (0.014 mols) of cupric chloride dihydrate was used instead of 3.2 g (0.014 mols) of nickel (II) chloride hexahydrate used in Example 1. Thus, 4.8 g of a dark green solid of 4-N,N-diethylsulfamoyl-1,2-benzenedithiol copper complex as a target substance was obtained. The yield was 42% with respect to 4-N,N-diethylsulfamoyl-1,2-dibromobenzene. The 4-N,N-diethylsulfamoyl-1,2-benzenedithiol copper complex thus obtained had a structural formula as shown below:

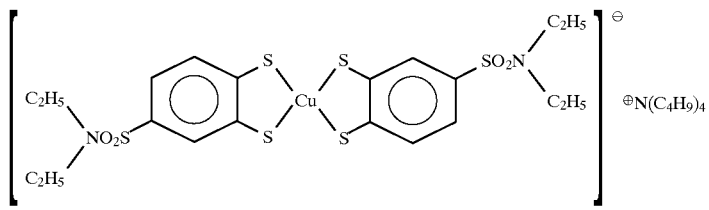

Analysis results and physical properties of the 4-N,N-diethylsulfamoyl-1,2-benzenedithiol copper complex thus obtained are shown below:

| HPLC 99.5% Elemental analysis | | | | | |
|---|---|---|---|---|---|
| | C | H | N | S | Cu |
| Calculated value | 50.46 | 7.29 | 4.90 | 22.45 | 7.42 |
| Measured value | 50.0 | 7.1 | 4.9 | 22.2 | 7.40 |

Melting point 31.2° C. (DSC)
Ultraviolet and visible absorption spectrum
(solvent: methylene chloride)
Maximum absorption wavelength (nm)  396.6, 339.0, 272.1, 251.0
Molar absorption coefficient   31948, 12897, 49481, 39319
Infrared absorption spectrum (KBr, cm$^{-1}$)
2961.2, 2932.3, 2872.5, 2361.4, 2332.5, 1537.0, 1440.6, 1356.7,
1327.8, 1155.2, 1114.7, 1014.4, 928.6, 813.8, 710.7, 693.3, 609.4
Solubility (g/100 g-MeOH 25° C.) 0.83 g

EXAMPLE 3

Preparation of Substituted Benzenedithiol Compound

First, 50 g of N,N-dimethylformamide, 1.2 g (0.022 mols) of iron powder and 0.4 g (0.013mols) of sulfur powder were added to 10 g (0.027 mols) of 4-N,N-diethylsulfamoyl-1,2-dibromobenzene prepared from a starting material of 1,2-dibromobenzene in substantially the same manner as in EXAMPLE 1, and then a solution containing 4.8 g (0.060 mols) of 70% sodium hydrosulfide dissolved in 50 g of N,N-dimethylformamide was added dropwise to the resulting mixture, and was allowed to react at 95° C. for 2 hours.

After the resulting reaction solution was cooled to room temperature, 240 g of monochlorobenzene and 60 g of water were added to the reaction solution. After being neutralized with hydrochloric acid, the resulting aqueous layer and organic layer were separated, and the aqueous layer was removed. In turn, a 2% sodium hydroxide aqueous solution was added to the organic layer. The resulting aqueous layer and organic layer were separated, and the organic layer was removed. Then, 6% sulfuric acid was added dropwise to the aqueous layer, and the resulting crystal was filtered out and dried. Thus, 6.0 g of 4-N,N-diethylsulfamoyl-1,2-benzenedithiol was obtained. The yield was 80% with respect to 4-N,N-diethylsulfamoyl-1,2-dibromobenzene.

The structural formula, analysis results and physical properties of 4-N,N-diethylsulfamoyl-1,2-benzenedithiol thus obtained are shown below:

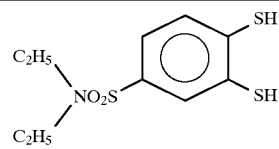

| Elemental analysis | | | | |
|---|---|---|---|---|
| | C | H | N | S |
| Calculated value | 43.29 | 5.45 | 5.05 | 34.67 |
| Measured value | 43.0 | 5.2 | 4.9 | 34.4 |
| HPLC | 99.4% | | | |
| NMR (CDCl$_3$) | | | | |
| δ | 7.2–6.8 ppm | (3H, m) | | |
| δ | 3.6 ppm | (1H, s) | | |
| δ | 3.5 ppm | (1H, s) | | |
| δ | 3.1 ppm | (4H, q) | | |
| δ | 1.1 ppm | (6H, t) | | |

EXAMPLE 4

Preparation of Substituted Benzenedithiol Complex

First, 5.5 g (0.020 mols) of 4-N,N-diethylsulfamoyl-1,2-benzenedithiol obtained in EXAMPLE 3 was dissolved in 24 g of methanol.

In turn, 23.8 g of a 10% sodium methylate-methanol solution (containing 0.044 mols of sodium methylate) was added dropwise to the resulting solution, which was stirred for 1 hour. Then, a solution containing 1.8 g (0.0076 mols) of nickel (II) chloride hexahydrate dissolved in 5.6 g of methanol was added dropwise to the resulting solution, and was allowed to react at 72° C. for 1 hour. After the reaction solution was cooled to room temperature, 10.3 g of a 31% tetrabutylammonium bromide-methanol solution (containing 0.0099 mols of tetrabutylammonium bromide) was added dropwise to the reaction solution, and was allowed to react for 2 hours at room temperature with stirring.

The resulting reaction solution was concentrated, and purified through silica gel column chromatography. Fractions were concentrated to give 5.7 g of a dark green solid of 4-N,N-diethylsulfamoyl-1,2-benzenedithiol nickel complex. The yield was 68% with respect to 4-N,N-diethylsulfamoyl-1,2-benzenedithiol.

EXAMPLE 5

Preparation of Substituted Benzenedithiol Metal Complex

A 300-ml four-neck flask equipped with a stirring device, a condenser and a thermometer was prepared. Then, 90 g of 1,2-ethylene dichloride and 45 g (0.19 mols) of 1,2-dibromobenzene were placed in the flask, and 53.5 g (0.20 mols) of 30% fuming sulfuric acid was added thereto dropwise in a gentle stream of nitrogen gas and allowed to react therewith at 70° C. for 2 hours. After the resulting reaction product solution was cooled, a reaction product was filtered out, and then dried. Thus, 57 g of crude 3,4-dibromobenzenesulfonic acid was obtained.

In turn, a 500-ml four-neck flask equipped with a stirring device, a condenser and a thermometer was prepared. Then, 57 g of the thus obtained crude 3,4-dibromobenzenesulfonic acid, 155 g of 1,2-ethylene dichloride and 18 g of N,N-dimethylformamide were placed in the flask, and 38 g (0.32 mols) of thionyl chloride was added thereto dropwise and allowed to react therewith at 60° to 65° C. for 1 hour. After being cooled to room temperature, the resulting reaction product solution was added dropwise to 300 g of water and stirred therein at 0° to 10° C. for 0.5 hours.

The aqueous layer and organic layer of the resulting reaction product solution were separated, and the aqueous layer was removed. Then, 35.7 g (0.42 mols) of piperidine was added dropwise to 191 g of the resulting organic layer, and was allowed to react at room temperature for 1 hour. In turn, 150 g of water was added to the resulting reaction product solution. Then, the resulting aqueous layer and organic layer were separated and, after the aqueous layer was removed, the solvent was distilled off under reduced pressure. Thus, 53.5 g of 4-piperidylsulfonyl-1,2-dibromobenzene was obtained. The yield was 73%.

Subsequently, 50 g of N,N-dimethylformamide, 0.8 g (0.014mols) of iron powder and 0.4 g (0.013mols) of sulfur powder were added to 10 g (0.026 mols) of 4-piperidylsulfonyl-1,2-dibromobenzene thus obtained. Then, a solution containing 4.6 g (0.057 mols) of 70% sodium hydrosulfide dissolved in 50 g of N,N-dimethylformamide was added dropwise to the resulting mixture, and was allowed to react at 100° C. for 2 hours.

In turn, 31.2 g of a 10% sodium methylate methanol solution (containing 0.057 mols of sodium methylate) was added dropwise to the resulting solution, which was stirred for 1 hour. Then, a solution containing 3.4 g (0.014 mols) of nickel (II) chloride hexahydrate dissolved in 10 g of methanol was added dropwise to the resulting solution, and was allowed to react at room temperature for 1 hour. Thereafter, 14.6 g of a 32% tetrabutylammonium bromide - methanol solution (containing 0.015 mols of tetrabutylammonium bromide) was added dropwise to the resulting solution, and was allowed to react for 2 hours at room temperature with stirring.

The resulting reaction solution was concentrated, and purified through silica gel column chromatography. Fractions were concentrated to give 1.8 g of a dark green solid of 4-piperidylsulfonyl-1,2-benzenedithiol nickel complex as a target substance. The yield was 16% with respect to 4-piperidylsulfonyl-1,2-dibromobenzene. The 4-piperidylsulfonyl-1,2-benzenedithiol nickel complex thus obtained had a structural formula as shown below:

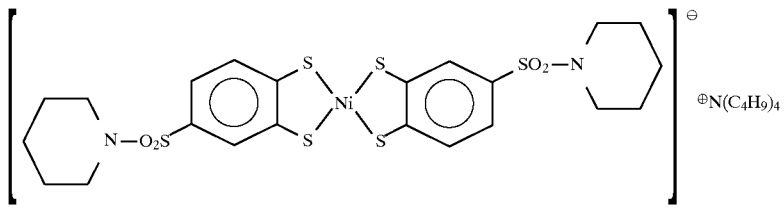

Analysis results and physical properties of the 4-piperidylsulfonyl-1,2-benzenedithiol nickel complex thus obtained are shown below:

| HPLC 99.5% | | | | |
|---|---|---|---|---|
| Elemental analysis | | | | |
| C | H | N | S | Ni |
| Calculated value 51.43 | 7.23 | 4.86 | 22.27 | 6.79 |
| Measured value 51.1 | 7.2 | 4.9 | 22.0 | 6.7 |

Melting point 150.9° C. (DSC)
Ultraviolet and visible absorption spectrum
(solvent: methylene chloride)
Maximum absorption wavelength (nm)   858.9, 369.7, 315.6, 258.6
Molar absorption coefficient              13138, 11968, 37383, 42094
Infrared absorption spectrum (KBr, cm$^{-1}$)
2940.9, 2852.2, 1467.6, 1355.7, 1336.4, 1297.9, 1166.7, 1103.1,
1099.2, 1053.0, 1051.0, 1039.0, 931.5, 819.6, 717.4, 615.2, 611.3

EXAMPLE 6

Preparation of Substituted Benzenedithiol Metal Complex

The preparation process was performed in substantially the same manner as in EXAMPLE 5 except that 2.5 g (0.015 mols) of cupric chloride dihydrate was used instead of 3.4 g of nickel (II) chloride hexahydrate used in Example 5. Thus, 5.1 g of a dark green solid of 4-piperidylsulfonyl-1,2-benzenedithiol copper complex as a target substance was obtained. The yield was 45% with respect to 4-piperidylsulfonyl-1,2-dibromobenzene. The 4-piperidylsulfonyl-1,2-benzenedithiol copper complex thus obtained had a structural formula as shown below:

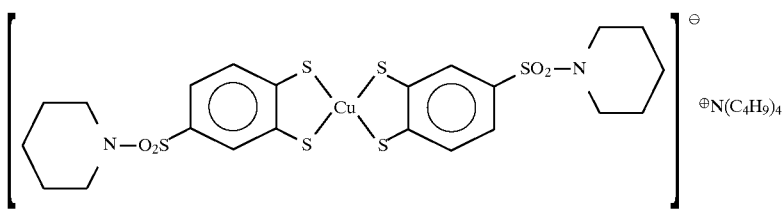

Analysis results and physical properties of the 4-piperidylsulfonyl-1,2-benzenedithiol copper complex thus obtained are shown below:

| HPLC 99.1% Elemental analysis | | | | | |
|---|---|---|---|---|---|
| | C | H | N | S | Cu |
| Calculated value | 51.17 | 7.19 | 4.84 | 22.15 | 7.32 |
| Measured value | 51.4 | 7.2 | 4.6 | 22.3 | 7.2 |

Melting point 140.9° C. (DSC)
Ultraviolet and visible absorption spectrum
(solvent: methylene chloride)
Maximum absorption wavelength (nm)  617.4, 396.7, 339.6, 272.7, 250.6
Molar absorption coefficient  318, 33995, 13805, 51874, 40348
Infrared absorption spectrum (KBr, cm$^{-1}$)
2961.2, 2858.3, 2940.5, 2340.0, 2854.2, 1551.5, 1468.5, 1443.5, 1355.7, 1337.4, 1336.4, 1166.7, 1116.6, 1095.4, 1051.0, 1035.6, 930.5, 813.8, 717.4, 616.1, 614.2, 611.3, 530.3

EXAMPLE 7

Preparation of Substituted Benzenedithiol Metal Complex

A 300-ml four-neck flask equipped with a stirring device, a condenser and a thermometer was prepared. Then, 90 g of 1,2-ethylene dichloride and 45 g (0.19 mols) of 1,2-dibromobenzene were placed in the flask, and 53.5 g (0.20 mols) of 30% fuming sulfuric acid was added thereto dropwise in a gentle stream of nitrogen gas and allowed to react therewith at 70° C. for 2 hours. After the resulting reaction product solution was cooled, a reaction product was filtered out, and then dried. Thus, 57 g of crude 3,4-dibromobenzenesulfonic acid was obtained.

In turn, a 500-ml four-neck flask equipped with a stirring device, a condenser and a thermometer was prepared. Then, 57 g of the thus obtained crude 3,4-dibromobenzenesulfonic acid, 155 g of 1,2-ethylene dichloride and 18 g of N,N-dimethylformamide were placed in the flask, and 38 g (0.32 mols) of thionyl chloride was added thereto dropwise and allowed to react therewith at 60° to 65° C. for 1 hour. After being cooled to room temperature, the resulting reaction product solution was added dropwise to 300 g of water and stirred therein at 0° to 10° C. for 0.5 hours.

The aqueous layer and organic layer of the resulting reaction product solution were separated, and the aqueous layer was removed. Then, 36.6 g (0.42 mols) of morpholine was added dropwise to 191 g of the resulting organic layer, and was allowed to react at room temperature for 1 hour. In turn, 150 g of water was added to the resulting reaction product solution. Then, the resulting aqueous layer and organic layer were separated and, after the aqueous layer was removed, the solvent was distilled off under reduced pressure. Thus, 54.9 g of 4-morpholinosulfonyl-1,2-dibromobenzene was obtained. The yield was 75%.

Subsequently, 50 g of N,N-dimethylformamide, 0.8 g (0.014 mols) of iron powder and 0.4 g (0.013mols) of sulfur powder were added to 10 g (0.026 mols) of 4-morpholinosulfonyl-1,2-dibromobenzene thus obtained. Then, a solution containing 4.6 g (0.057 mols) of 70% sodium hydrosulfide dissolved in 50 g of N,N-dimethylformamide was added dropwise to the resulting mixture, and was allowed to react at 100 C for 2 hours.

In turn, 31.2 g of a 10% sodium methylate - methanol solution (containing 0.057 mols of sodium methylate) was added dropwise to the resulting solution, which was stirred for 1 hour. Then, a solution containing 2.5 g (0.015 mols) of cupric chloride dihydrate dissolved in 10 g of methanol was added dropwise to the resulting solution, and was allowed to react at room temperature for 1 hour. Thereafter, 14.6 g of a 32% tetrabutylammonium bromide - methanol solution (containing 0.015 mols of tetrabutylammonium bromide) was added dropwise to the reaction solution, and was allowed to react for 2 hours at room temperature with stirring.

The resulting reaction solution was concentrated, and purified through silica gel column chromatography. Fractions were concentrated to give 4.8 g of a dark green solid of 4-morpholinosulfonyl-1, 2-benzenedithiol copper complex as a target substance. The yield was 42% with respect to 4-morpholinosulfonyl-1,2-dibromobenzene. The 4-morpholinosulfonyl-1,2-benzenedithiol copper complex thus obtained had a structural formula as shown below:

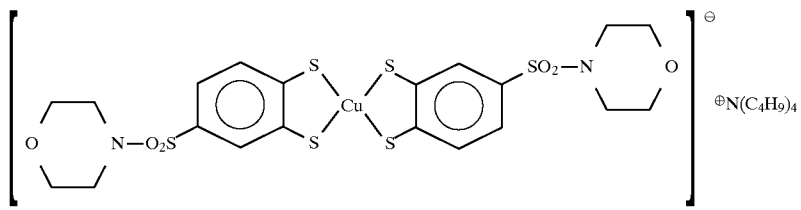

Analysis results and physical properties of the 4-morpholinosulfonyl-1,2-benzenedithiol copper complex thus obtained are shown below:

| HPLC 99.5% Elemental analysis | | | | | |
|---|---|---|---|---|---|
| | C | H | N | S | Cu |
| Calculated value | 48.87 | 6.61 | 4.75 | 21.74 | 7.18 |
| Measured value | 48.5 | 6.6 | 4.8 | 21.6 | 7.1 |
| Maximum absorption wavelength (nm) 395.6, 339.6, 273.4, 251.0 | | | | | |
| Molar absorption coefficient 35100, 14200, 53200, 39900 | | | | | |
| Infrared absorption spectrum (KBr, cm$^{-1}$) | | | | | |
| 3448.1, 2960.2, 2931.3, 2858.0, 1550.5, 1448.3, 1382.7, 1344.2, | | | | | |
| 1294.0, 1261.2, 1238.1, 1166.7, 1114.7, 1070.3, 1035.6, 943.0, | | | | | |
| 883.3, 852.4, 815.8, 725.1, 680.8, 624.8, 609.4, 561.2, 532.3, 497.6 | | | | | |

EXAMPLE 8

Preparation of Substituted Benzenedithiol Compound

First, 50 g of N,N-dimethylformamide, 0.8 g (0.014 mols) of iron powder and 0.4 g (0.013mols) of sulfur powder were added to 10 g (0.026 mols) of 4-piperidylsulfonyl-1,2-dibromobenzene prepared from a starting material of 1,2-dibromobenzene in substantially the same manner as in EXAMPLE 5, and then a solution containing 4.6 g (0.057 mols) of 70% sodium hydrosulfide dissolved in 50 g of N,N-dimethylformamide was added dropwise to the resulting mixture, and was allowed to react at 100° C. for 2 hours.

After the resulting reaction solution was cooled to room temperature, 120 g of monochlorobenzene and 30 g of water were added to the reaction solution. After being neutralized with hydrochloric acid, the resulting aqueous layer and organic layer were separated, and the aqueous layer was removed. In turn, a 2% sodium hydroxide solution was added to the organic layer. The resulting aqueous layer and organic layer were separated, and the organic layer was removed. Then, 6% sulfuric acid was added dropwise to the aqueous layer, and the resulting crystal was filtered out and dried. Thus, 5.6 g of 4-piperidylsulfonyl-1,2-benzenedithiol was obtained. The yield was 54% with respect to 1,2-dibromobenzene.

The structural formula, analysis results and physical properties of 4-piperidylsulfonyl-1,2-benzenedithiol thus obtained are shown below:

| Elemental analysis | | | | |
|---|---|---|---|---|
| | C | H | N | S |
| Calculated value | 45.65 | 5.22 | 4.84 | 33.24 |
| Measured value | 45.9 | 5.0 | 4.7 | 33.6 |
| HPLC | 98.8% | | | |
| NMR (CDCl$_3$) | | | | |
| δ | 1.48 ppm | (6H, m) | | |
| δ | 3.00 ppm | (4H, m) | | |
| δ | 3.83 ppm | (1H, s) | | |
| δ | 3.91 ppm | (1H, s) | | |
| δ | 7.1–7.4 ppm | (3H, m) | | |

EXAMPLE 9

Preparation of Substituted Benzenedithiol Complex

First, 5 g (0.017 mols) of 4-piperidylsulfonyl-1,2-benzenedithiol obtained in Example 8 was dissolved in 20 g of methanol.

In turn, 20 g of a 10% sodium methylate - methanol solution (containing 0.037 mols of sodium methylate) was added dropwise to the resulting solution, which was stirred for 1 hour. Then, a solution containing 2.0 g (0.0084 mols) of nickel (II) chloride hexahydrate dissolved in 15 g of methanol was added dropwise to the resulting solution, and was allowed to react at room temperature for 1 hour. Thereafter, 9.0 g of a 30% tetrabutylammonium bromide - methanol solution (containing 0.0084 mols of tetrabutylammonium bromide) was added dropwise to the reaction solution, and was allowed to react for 24 hours at room temperature with stirring.

The resulting reaction solution was concentrated, and purified through silica gel column chromatography. Fractions were concentrated to give 1.6 g of a dark green solid of 4-piperidylsulfonyl-1,2-benzenedithiol nickel complex. The yield was 21% with respect to 4-piperidylsulfonyl-1,2-benzenedithiol.

EXAMPLE 10

Preparation of Substituted Benzenedithiol Compound

First, 50 g of N,N-dimethylformamide, 0.8 g (0.014 mols) of iron powder and 0.4 g (0.013mols) of sulfur powder were added to 10 g (0.026 mols) of 4-morpholinosulfonyl-1,2-dibromobenzene prepared from a starting material of 1,2- dibromobenzene in substantially the same manner as in EXAMPLE 7, and then a solution containing 4.6 g (0.057 mols) of 70% sodium hydrosulfide dissolved in 50 g of N,N-dimethylformamide was added dropwise to the resulting mixture, and was allowed to react at 100° C. for 2 hours.

After the resulting reaction solution was cooled to room temperature, 120 g of monochlorobenzene and 30 g of water were added to the reaction solution. After being neutralized with hydrochloric acid, the resulting aqueous layer and organic layer were separated, and the aqueous layer was removed. In turn, a 2% sodium hydroxide aqueous solution was added to the organic layer. The resulting aqueous layer and organic layer were separated, and the organic layer was removed. Then, 6% sulfuric acid was added dropwise to the aqueous layer, and the resulting crystal was filtered out and dried. Thus, 3.9 g of 4-morpholinosulfonyl-1,2-benzenedithiol was obtained. The yield was 39% with respect to 1,2-dibromobenzene.

The structural formula, analysis results and physical properties of 4-morpholinosulfonyl-1,2-benzenedithiol thus obtained are shown below:

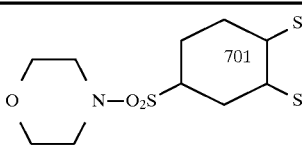

| | Elemental analysis | | | |
|---|---|---|---|---|
| | C | H | N | S |
| Calculated value | 41.22 | 4.50 | 4.81 | 33.01 |
| Measured value | 41.7 | 4.4 | 4.6 | 33.5 |

| HPLC | 99.1% | |
|---|---|---|
| NMR (CDCl$_3$) | | |
| δ | 3.15 ppm | (4H, t) |
| δ | 3.60 ppm | (4H, t) |
| δ | 3.82 ppm | (1H, s) |
| δ | 3.92 ppm | (1H, s) |
| δ | 7.1–7.4 ppm | (3H, m) |

EXAMPLE 11

Preparation of Substituted Benzenedithiol Metal Complex

A 300-ml four-neck flask equipped with a stirring device, a condenser and a thermometer was prepared. Then, 80 g of 1,2-ethylene dichloride and 51 g (0.22 mols) of 1,2-dibromobenzene were placed in the flask, and 38 g (0.29 mols) of 60% fuming sulfuric acid was added thereto dropwise in a gentle stream of nitrogen gas and allowed to react therewith at 70° C. for 2 hours. After the resulting reaction product solution was cooled, a reaction product was filtered out, and then dried. Thus, 51 g of crude 3,4-dibromobenzenesulfonic acid was obtained.

In turn, a 500-ml four-neck flask equipped with a stirring device, a condenser and a thermometer was prepared. Then, 51 g of the thus obtained crude 3,4-dibromobenzenesulfonic acid, 155 g (1.98 mols) of benzene and 20 g of N,N-dimethylformamide were placed in the flask, and 27 g (0.23 mols) of thionyl chloride was added thereto dropwise and allowed to react therewith at 60° to 65° C. for 1 hour. After being cooled to room temperature, the resulting reaction product solution was added dropwise to 300 g of water and stirred therein at 0° to 10° C. for 0.5 hours.

The aqueous layer and organic layer of the resulting reaction product solution were separated, and the aqueous layer was removed. Then, 28 g (0.21 mols) of aluminum chloride was added to 280 g of the resulting organic layer, and was allowed to react at 75° C. for 1 hour. In turn, 300 g of water was added to the resulting reaction product solution. Then, the resulting aqueous layer and organic layer were separated and, after the aqueous layer was removed, the solvent was distilled off under reduced pressure. Thus, 38 g of 4-phenylsulfonyl-1,2-dibromobenzene was obtained. The yield was 47%.

The structural formula, analysis results and physical properties of 4-phenylsulfonyl-1,2-dibromobenzene thus obtained are shown below:

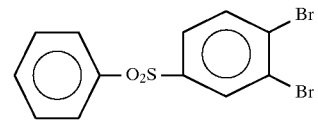

| | Elemental analysis | | | |
|---|---|---|---|---|
| | C | H | S | Br |
| Calculated value | 38.33 | 2.14 | 8.53 | 42.49 |
| Measured value | 38.2 | 2.2 | 8.4 | 42.6 |

| HPLC | 99.2% | |
|---|---|---|
| Melting point | 134.7° C. (DSC) | |
| NMR (CDCl$_3$) | | |
| δ | 7.4–6.8 ppm | (8H, m) |

Subsequently, 35 g of N,N-dimethylformamide, 0.7 g (0.013 mols) of iron powder and 0.3 g (0.0094 mols) of sulfur powder were added to 5.1 g (0.014 mols) of 4-phenylsulfonyl-1,2-dibromobenzene thus obtained. Then, a solution containing 2.5 g (0.031 mols) of 70% sodium hydrosulfide dissolved in 25 g of N,N-dimethylformamide was added dropwise to the resulting mixture, and was allowed to react at 95° C. for 2 hours.

In turn, 15.6 g of a 11% sodium methylate - methanol solution (containing 0.0285 mols of sodium methylate) was added dropwise to the resulting solution, which was stirred for 1 hour. Then, a solution containing 1.7 g (0.0072 mols) of nickel (II) chloride hexahydrate dissolved in 6 g of methanol was added dropwise to the resulting solution, and was allowed to react at 72° C. for 1 hour. After the reaction solution was cooled to room temperature, 9.3 g of a 25% tetrabutylammonium bromide - methanol solution (containing 0.0071 mols of tetrabutylammonium bromide) was added dropwise to the reaction solution, and was allowed to react for 2 hours at room temperature with stirring.

The resulting reaction solution was concentrated, and purified through silica gel column chromatography. Fractions were concentrated to give 2.8 g of a dark green solid of 4-phenylsulfonyl-1,2-benzenedithiol nickel complex as a target substance. The yield was 48% with respect to 4-phenylsulfonyl-1,2-dibromobenzene. The 4-phenylsulfonyl-1,2-benzenedithiol nickel complex thus obtained had a structural formula as shown below:

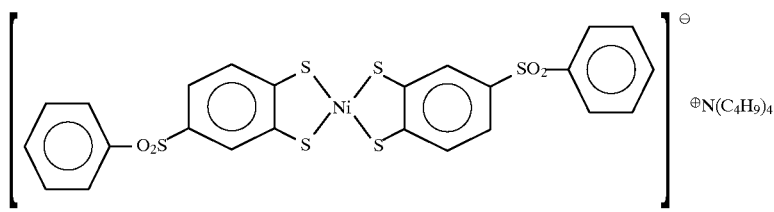

Analysis results and physical properties of the 4-phenylsulfonyl-1, 2-benzenedithiol nickel complex thus obtained are shown below:

HPLC 96.9%
Elemental analysis

|  | C | H | N | S | Ni |
|---|---|---|---|---|---|
| Calculated value | 55.74 | 6.08 | 1.62 | 22.32 | 6.81 |
| Measured value | 55.1 | 5.9 | 1.6 | 23.0 | 6.5 |

Melting point 167.9° C. (DSC)
Ultraviolet and visible absorption spectrum
(solvent: methylene chloride)
Maximum absorption wavelength (nm)   861.4, 444.6, 316.9, 261.2
Molar absorption coefficient   13394, 29829, 39695, 35217
Infrared absorption spectrum (KBr, $cm^{-1}$)
2958.3, 2871.5, 2361.4, 2338.3, 1551.5, 1445.4, 1307.5, 1157.1, 1107.9, 1071.3, 1039.5, 821.5, 722.2, 686.5, 619.1, 589.2

EXAMPLE 12

Preparation of Substituted Benzenedithiol Metal Complex

The preparation process was performed in substantially the same manner as in EXAMPLE 11 except that 1.2 g (0.0070 mols) of cupric chloride dihydrate was used instead of 1.7 g of nickel (II) chloride hexahydrate used in Example 11. Thus, 3.3 g of a dark green solid of 4-phenylsulfonyl-1,2-benzenedithiol copper complex as a target substance was obtained. The yield was 57% with respect to 4-phenylsulfonyl-1,2-dibromobenzene. The 4-phenylsulfonyl-1, 2-benzenedithiol copper complex thus obtained had a structural formula as shown below:

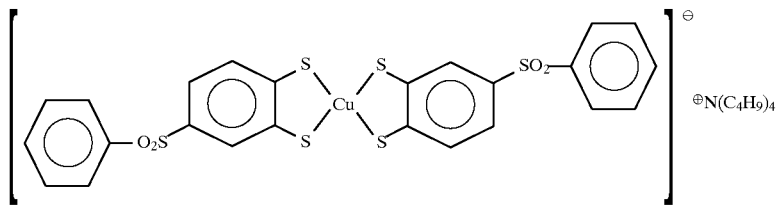

Analysis results and physical properties of the 4-phenylsulfonyl-1, 2-benzenedithiol copper complex thus obtained are shown below:

HPLC 99.3%
Elemental analysis

|  | C | H | N | S | Cu |
|---|---|---|---|---|---|
| Calculated value | 55.43 | 6.05 | 1.61 | 22.20 | 7.3 |
| Measured value | 55.4 | 6.1 | 1.9 | 22.3 | 7.2 |

Melting point 38.0° C. (DSC)
Ultraviolet and visible absorption spectrum
(solvent: methylene chloride)
Maximum absorption wavelength (nm)   600.7, 395.0, 347.0, 283.8, 253.8, 227.6
Molar absorption coefficient   390, 37095, 15557, 44969, 35117, 32280
Infrared absorption spectrum (KBr, $cm^{-1}$)
2959.3, 2872.5, 2361.4, 2336.4, 1539.9, 1444.4, 1359.6, 1305.6, 1156.1, 1117.6, 1116.6, 1071.3, 1034.6, 816.7, 722.2, 680.8, 618.1, 588.2

EXAMPLE 13

Preparation of Substituted Benzenedithiol Compound

First, 35 g of N,N-dimethylformamide, 0.7 g (0.013 mols) of iron powder and 0.3 g (0.0094 mols) of sulfur powder were added to 5 g (0.013 mols) of 4-phenylsulfonyl-1,2-dibromobenzene prepared from a starting material of 1,2-dibromobenzene in substantially the same manner as in EXAMPLE 11, and then a solution containing 2.5 g (0.031 mols) of 70% sodium hydrosulfide dissolved in 25 g of N,N-dimethylformamide was added dropwise to the resulting mixture, and was allowed to react at 95° C. for 2 hours.

After the resulting reaction solution was cooled to room temperature, 120 g of monochlorobenzene and 30 g of water were added to the reaction solution. After being neutralized with hydrochloric acid, the resulting aqueous layer and organic layer were separated, and the aqueous layer was removed. In turn, a 2% sodium hydroxide aqueous solution was added to the resulting organic layer. The resulting aqueous layer and organic layer were separated, and the organic layer was removed. Then, 6% sulfuric acid was added dropwise to the aqueous layer, and the resulting crystal was filtered out and dried. Thus, 3.0 g of 4-phenylsulfonyl-1,2-benzenedithiol was obtained. The yield was 80% with respect to 1,2-dibromobenzene.

The structural formula, analysis results and physical properties of 4-phenylsulfonyl-1,2-benzenedithiol thus obtained are shown below:

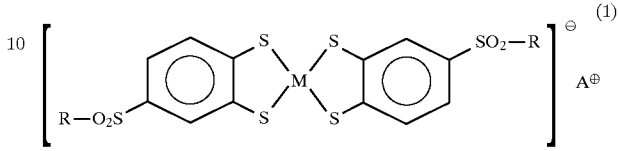

Elemental analysis

|  | C | H | S |
|---|---|---|---|
| Calculated value | 51.03 | 3.57 | 34.06 |
| Measured value | 50.9 | 3.6 | 34.1 |

| HPLC | 98.8% | |
|---|---|---|
| NMR (CDCl₃) | | |
| δ | 7.2–6.8 ppm | (8H, m) |
| δ | 3.7 ppm | (1H, s) |
| δ | 3.6 ppm | (1H, s) |

EXAMPLE 14

Preparation of Substituted Benzenedithiol Metal Complex

First, 2.5 g (0.0089 mols) of 4-phenylsulfonyl-1,2-benzenedithiol obtained in EXAMPLE 13 was dissolved in 10 g of methanol.

In turn, 10. 5 g of a 10% sodium methylate - methanol solution (containing 0.0194 mols of sodium methylate) was added dropwise to the resulting solution, which was stirred for 1 hour. Then, a solution containing 1.1 g (0.0046 mols) of nickel (II) chloride hexahydrate dissolved in 5.0 g of methanol was added dropwise to the resulting solution, and was allowed to react at 72° C. for 1 hour. After the reaction solution was cooled to room temperature, 4.8 g of a 31% tetrabutylammonium bromide - methanol solution (containing 0.0046 mols of tetrabutylammonium bromide) was added dropwise to the reaction solution, and was allowed to react for 2 hours at room temperature with stirring.

The resulting reaction solution was concentrated, and purified through silica gel column chromatography. Fractions were concentrated to give 1.8 g of a dark green solid of 4-phenylsulfonyl-1,2-benzenedithiol nickel complex. The yield was 47% with respect to 4-phenylsulfonyl-1,2-benzenedithiol.

The present invention can be embodied in any other ways without departing from the sprit and principal features thereof. The examples described above are merely illustrative of the present invention in any aspect but not limitative of the same. The scope of the invention is defined only by the appended claims and therefore is not limited by the specification herein set forth. It should be understood that variations and modifications within the equivalents of the claims are to fall within the scope of the present invention.

We claim:

1. A substituted benzenedithiol metal complex represented by the general formula (1):

wherein M is a transition metal; $A^+$ is a quaternary ammonium group; and R is an organic group selected from the group consisting of organic groups represented by the formulae (i), (ii), (iii) and (iv):

(wherein R is an alkyl group having 1 to 4 carbon atoms),

(wherein n is 3, 4 or 5),

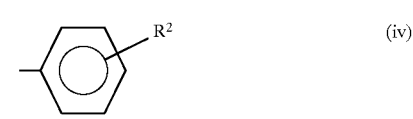

(wherein $R^2$ is one of a hydrogen atom and a substituent having 1 to 4 carbon atoms).

2. The substituted benzenedithiol metal complex according to claim 1, wherein the transition metal is one of copper, cobalt and nickel.

3. The substituted benzenedithiol metal complex according to claim 1, wherein the quaternary ammonium group is one of tetra-n-butylammonium group, tetraethylammonium group, tetraphenylammonium group, tetrabenzylammonium group and trimethylbenzylammonium group.

4. The complex according to claim 1 being a 4-N,N-diethylsulfamoyl-1,2-benzenedithiol metal complex represented by the general formula (1-a):

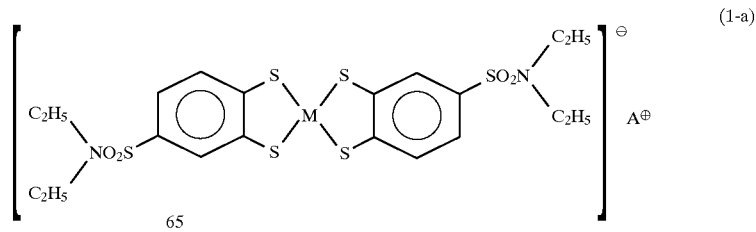

wherein M is a transition metal; and A⁺ is a quaternary ammonium group.

5. The complex according to claim 1 being a 4-piperidylsulfonyl-1,2-benzenedithiol metal complex represented by the general formula (1-b):

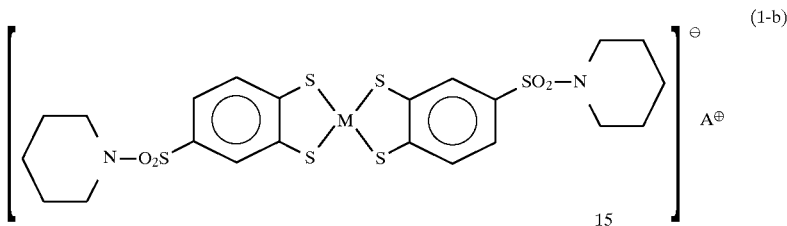

wherein M is a transition metal; and A⁺ is a quaternary ammonium group.

6. The complex according to claim 1 being a 4-morpholinosulfonyl-1,2-benzenedithiol metal complex represented by the general formula (1-c):

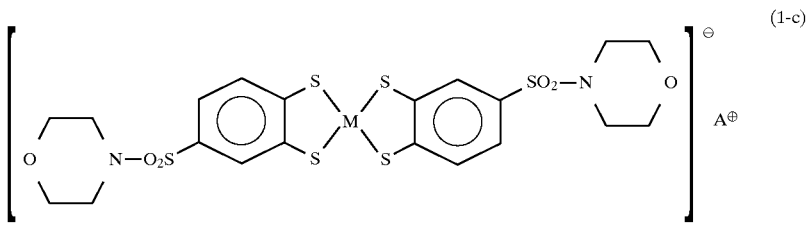

wherein M is a transition metal; and A⁺ is a quaternary ammonium group.

7. The complex according to claim 1 being a 4-phenylsulfonyl-1,2-benzenedithiol metal complex represented by the general formula (1-d):

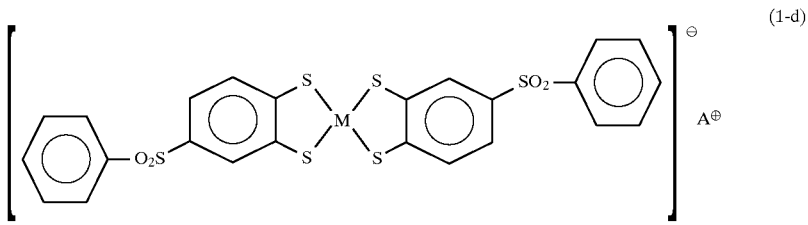

wherein M is a transition metal; and A⁺ is a quaternary ammonium group.

8. A process for preparing a substituted benzenedithiol metal complex represented by the general formula (1):

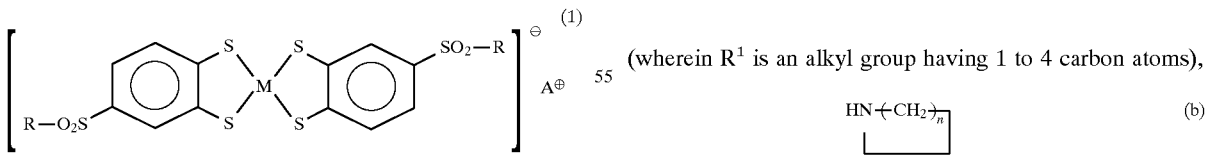

wherein R is the same as in the general formula (2); M is a transition metal; and A⁺ is a quaternary ammonium group, the process comprising the steps of:

reacting 3,4-dibromobenzenesulfonyl chloride with a compound selected from the group consisting of compounds represented by the general formulae (a), (b), (c) and (d) to synthesize a 4-substituted sulfonyl-1,2-dibromobenzene represented by the general formula (2):

(wherein $R^1$ is an alkyl group having 1 to 4 carbon atoms),

(wherein n is 3, 4 or 5),

-continued

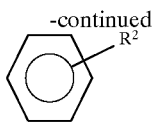

(wherein R² is one of a hydrogen atom and a substitutent having 1 to 4 carbon atoms),

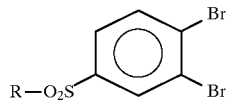

wherein R is an organic group selected from the group consisting of organic groups represented by the formulae (i), (ii), (iii) and (iv):

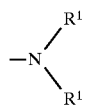

(wherein R¹ is an alkyl group having 1 to 4 carbon atoms), $$-N\!\!+\!\!CH_2\!\!+\!\!_n \quad \text{(ii)}$$

(wherein n is 3, 4 or 5),

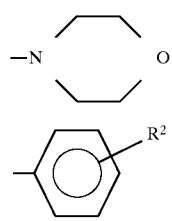

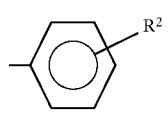

(wherein R² is one of a hydrogen atom and a substituent having 1 to 4 carbon atoms);
converting the 4-substituted sulfonyl-1,2-dibromobenzene into a 4-substituted sulfonyl-1,2-benzenedithiol represented by the general formula (3):

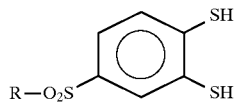

wherein R is the same as in the general formula (2); and
reacting the 4-substituted sulfonyl-1,2-benzenedithiol with a salt of the transition metal and a salt of the quaternary ammonium.

9. The substituted benzenedithiol metal complex preparation process according to claim 8, wherein the 4-substituted sulfonyl-1,2-dibromobenzene is reacted with sodium hydrosulfide in the presence of catalysts of iron powder and sulfur powder in the step of converting the 4-substituted sulfonyl-1,2-dibromobenzene into the 4-substituted sulfonyl-1,2-benzenedithiol.

10. The substituted benzenedithiol metal complex preparation process according to claim 8, wherein the transition metal salt is one of a salt of copper, a salt of cobalt and a salt of nickel.

11. The substituted benzenedithiol metal complex preparation process according to claim 8, wherein the quaternary ammonium salt is one of a tetra-n-butylammonium salt, a tetraethylammonium salt, a tetraphenylammonium salt, a tetrabenzylammonium salt and trimethylbenzylammonium salt.

12. The substituted benzenedithiol metal complex preparation process according to claim 8, wherein the 4-substituted sulfonyl-1,2-benzenedithiol is reacted with the transition metal salt and the quaternary ammonium salt in the presence of an alkoxide.

13. A process for preparing a substituted benzenedithiol metal complex represented by the general formula (1):

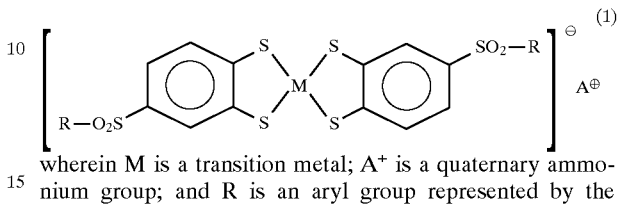

wherein M is a transition metal; A⁺ is a quaternary ammonium group; and R is an aryl group represented by the formula (iv):

(wherein R² is one of a hydrogen atom and a substitutent having 1 to 4 carbon atoms), the process comprising the steps of:
preparing a solution by dissolving 3,4-dibromobenzenesulfonyl chloride in a compound represented by the formula (d):

wherein R² is one of a hydrogen atom and a substituent having 1 to 4 carbon atoms;
adding aluminum chloride to the solution and reacting 3,4-dibromobenzenesulfonyl chloride with the compound represented by the general formula (d) to synthesize 4-arylsulfonyl-1,2-dibromobenzene;
converting the 4-arylsulfonyl-1,2-dibromobenzene into 4-arylsulfonyl-1,2-benzenedithiol; and
reacting the 4-arylsulfonyl-1,2-benzenedithiol with a salt of the transition metal and a salt of the quaternary ammonium.

14. A process for preparing a substituted benzenedithiol metal complex represented by the general formula (1):

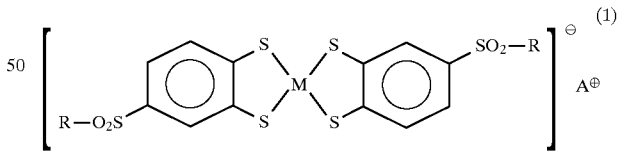

wherein R is the same as in the general formula (3); M is a transition metal; and A⁺ is a quaternary ammonium group, the process comprising the step of reacting a substituted benzenedithiol compound represented by the general formula (3) with a salt of the transition metal and a salt of the quaternary ammonium:

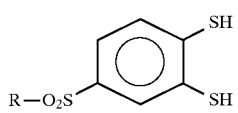

wherein R is an organic group selected from the group consisting of organic groups represented by the formulae (i), (ii), (iii) and (iv):

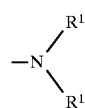  (i)

(wherein R¹ is an alkyl group having 1 to 4 carbon atoms),

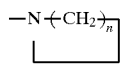  (ii)

(wherein n is 3, 4 or 5),

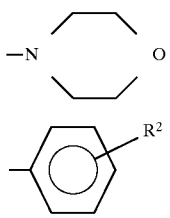  (iii)

(iv)

(wherein R² is one of a hydrogen atom and a substitutent having 1 to 4 carbon atoms).

15. A composition comprising a substituted benzenedithiol metal complex represented by the general formula (1) as a singlet oxygen quencher:

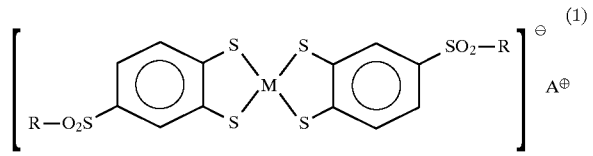  (1)

wherein M is a transition metal; A⁺ is a quaternary ammonium group; and R is an organic group selected from the group consisting of organic groups represented by the formulae (i), (ii), (iii) and (iv):

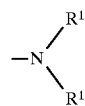  (i)

(wherein R¹ is an alkyl group having 1 to 4 carbon atoms),

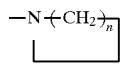  (ii)

(wherein n is 3, 4 or 5),

  (iii)

(iv)

(wherein R² is one of a hydrogen atom and a substituent having 1 to 4 carbon atoms; and an indolenine cyanine dye.

16. An optical data recording medium comprising a substituted benzenedithiol metal complex represented by the general formula (1):

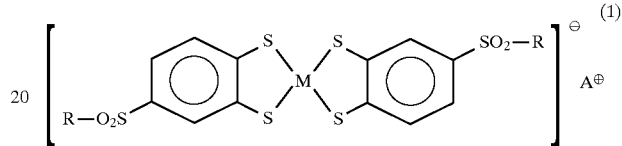  (1)

wherein M is a transition metal; A⁺ is a quaternary ammonium group; and R is an organic group selected from the group consisting of organic groups represented by the formulae (i), (ii), (iii) and (iv):

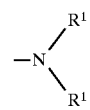  (i)

(wherein R¹ is an alkyl group having 1 to 4 carbon atoms),

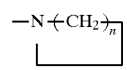  (ii)

(wherein n is 3, 4 or 5),

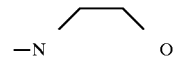  (iii)

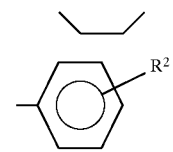  (iv)

(wherein R² is one of a hydrogen atom and a substituent having 1 to 4 carbon atoms).

* * * * *